United States Patent [19]

Redmond, Jr.

[11] 4,312,878

[45] Jan. 26, 1982

[54] METHOD OF ELIMINATING OPIATE WITHDRAWAL SYMPTOMS WITH CLONIDINE IN HUMANS

[75] Inventor: Donald E. Redmond, Jr., Hamden, Conn.

[73] Assignee: Boehringer Ingelheim International GmbH, Ingelheim am Rhein, Fed. Rep. of Germany

[21] Appl. No.: 168,258

[22] Filed: Jul. 10, 1980

Related U.S. Application Data

[63] Continuation of Ser. No. 33,943, Apr. 27, 1979, abandoned.

[51] Int. Cl.³ ............................................. A61K 31/415
[52] U.S. Cl. ................................................. 424/273 R
[58] Field of Search ..................................... 424/273 R

[56] References Cited

PUBLICATIONS

Gold et al., Lancet, Apr. 29, 1978, pp. 929–930; Sep. 16, 1978, pp. 599–601.
Chem. Abst. (S), 88—411 B (1978).

Primary Examiner—Stanley J. Friedman
Attorney, Agent, or Firm—Hammond & Littell, Weissenberger & Muserlian

[57] ABSTRACT

A method of eliminating opiate withdrawal symptoms in human opiate addicts by oral administration of clonidine.

2 Claims, No Drawings

METHOD OF ELIMINATING OPIATE WITHDRAWAL SYMPTOMS WITH CLONIDINE IN HUMANS

This is a continuation of copending application Ser. No. 33,943, filed Apr. 27, 1979, now abandoned.

This invention relates to a novel method of eliminating opiate withdrawal symptoms in human opiate addicts by oral administration of 2-(2,6-dichloro-anilino)-2-imidazoline (generic name—clonidine) or a non-toxic pharmaceutically acceptable acid addition salt thereof.

BACKGROUND OF THE INVENTION

Because opiates seem to have behavioral and biochemical effects which involve interaction with catecholamine neurotransmitter systems, clinicians have tried to modify opiate euphoria and withdrawal by giving drugs which modify these neurotransmitters. This approach has not met with any great success, and the usual treatment for opiate withdrawal is replacement with methadone followed by a period of maintenance for psychosocial rehabilitation and then detoxification or gradual withdrawal. However, detoxification from methadone maintenance is a slow and difficult process, and the patients frequently experience minor abstinence symptoms. Opiate agonists will block withdrawal symptoms, but have their own potential for abuse and withdrawal symptoms. A non-opiate treatment which could control symptoms during acute opiate withdrawal would be welcome.

Studies in rodents and primates suggest that the neurotransmitter noradrenaline (norepinephrine) is involved in opiate withdrawal, and my early experience with clonidine supports a noradrenergic mediation of opiate withdrawal.

OBJECTS OF THE INVENTION

It is an object of the present invention to provide a method of effectively eliminating opiate withdrawal symptoms in humans with the aid of an agent which itself is a non-opiate.

Other objects and advantages of the invention will become apparent as the description thereof proceeds.

DESCRIPTION OF THE INVENTION

I have discovered that the above object is achieved by orally administering 5 to 15 $\mu$g/kg of clonidine to human opiate addicts after withdrawal from chronic methadone treatment.

The patients were members in good standing of the Substance Abuse Unit treatment program of the Yale University School of Medicine and the Connecticut Mental Health Center. They had been addicted to opiates for 6–10 years and to methadone for 6–60 months. All expressed interest in discontinuing methadone, and all gave informed consent to the study which required a 2-day phased withdrawal from methadone before admission to the research unit and at least 36 hours with no opiate administration. All had objective signs of opiate withdrawal and urine specimens showing only residual methadone. The patients were observed for withdrawal signs and symptoms by a research nurse every 30 minutes from 8 A.M. while the patients were at bed rest. The nurse rated twenty-one items associated with the withdrawal as present (1) or absent (0) the score being added to give a measure of withdrawal severity. The symptoms and signs were: craving, anxiety, yawning, perspiration, lacrimation, rhinorrhea, "yen sleep", mydriasis, gooseflesh, tremors, hot and cold flashes, aching bones and muscles, anorexia, increased blood-pressure, insomnia, increased temperature, increased respiratory-rate and depth, increased pulse-rate, restlessness, nausea, vomiting, diarrhea, and spontaneous orgasm. All patients completed self-rating analogue scales every 30 min. from 9 A.M. until 5 P.M. to assess changes in nervousness, being "high", unpleasantness, energy, and irritability. At 11 A.M. and 1 P.M. the patients took 5 $\mu$g/kg, clonidine or placebo orally in matching vehicles. The experiments were randomized and double blind, patient, nurse, and physician being unaware of the order of administration.

The number of withdrawal signs increased during the baseline period, but after clonidine the withdrawal score fell to almost zero from 14.0$\pm$0.6 S.E.M. to 0.5$\pm$0.2 at 90 minutes (paired t=20.7; P<0.01) and to 0.2$\pm$0.1 at 120 minutes. Systolic blood pressure fell from a pretreatment means of 124$\pm$3 to 106$\pm$3 (P<0.01), as did diastolic pressure 85$\pm$3 to 69$\pm$3, (P<0.01), 120 minutes after clonidine administration.

Relief of subjective distress was also dramatic. On the self-rating scales, where 70 is the highest score, there were significant decreases in self-rated "nervousness" from 57$\pm$4 before treatment to 27$\pm$2 at 120 minutes, and "irritability" (47$\pm$3 to 24$\pm$2.0), and both "nervousness" and "irritability ratings remained significantly decreased from 90 minutes after clonidine administration until discharge. "Energy" was unchanged nor did the self-rated "high" scale alter significantly. There were significant decreases on both "unpleasantness" and "uninvolved" scales. All eleven patients felt that they were "kicking" on admission, but not after clonidine administration. Placebo had no significant effects on any of the measurements or ratings.

Ten patients were offered clonidine alone on discharge in an open pilot study of clonidine effects over a longer period and under more realistic conditions. All chose it over a return to methadone. One man chose outpatient clonidine but, in accordance with my original protocol received 5 mg of methadone in addition (a reduction of 20 mg/day). The patients were given 5 $\mu$g/kg clonidine to take orally twice daily for a week. Each day urines were screened for opiates, vital signs were checked, and nurses' abstinence ratings and self-ratings were done. There were no significant changes in the abstinence ratings during the outpatient trial. The only complaints were occasional sluggishness and occasional difficulty in falling or staying asleep. When outpatient clonidine was stopped, nine patients had been without their usual methadone doses for 12 days or more. Several patients did not take their clonidine as directed, some thinking that they felt so good that it was not necessary. One patient, whose husband was selling and using heroin, left the hospital and did not take her clonidine for over 36 hours, experienced some withdrawal symptoms, and took a single dose of heroin before being put on a 5 mg dose of methadone on the 4th day after the last methadone. At the end of the one-week trail of clonidine in the remaining nine patients, all were without significant changes in the nurse-rated abstinence signs. All had urines showing no signs of opiate use.

Clonidine was discontinued at the end of the week, producing no evidence of chonidine withdrawal symptoms and no evidence of any exacerbation in opiate withdrawal symptoms. These patients were closely followed up by their counsellors, the research nurse, and the physician, with supervised "random" urines at least once weekly for six months. It is too early to evaluate the effects of brief clonidine treatment on permanent abstinence from opiates. However, this pilot study suggests that clonidine had a striking effect on opiate withdrawal, and during the period of outpatient clonidine administration most patients continued to do well.

Six weeks or more after clonidine discontinuation four of the eleven patients had returned to methadone maintenance at reduced doses (5–10 mg). These patients admitted using heroin at least once. Two attributed their failure to remain drug-free to the role of maintenance methadone in helping them to think of themselves as "without the ability to get high". The other two patients had major depressive episodes by research diagnostic criteria—depressed mood, sleep, disorders, and decreased concentration, energy, appetite, interest, and libido 3–6 weeks after discontinuation of methadone. One was psychotic and agitated and the other was suicidal. Both of these patients had previously been admitted to psychiatric hospital for depression. Their depressive episodes were aborted by reintroduction of methadone at reduced doses (5–10 mg daily). In another patient, who is still opiate-free, panic anxiety attacks which pre-dated his initial drug addiction recurred. So far he has been successfully treated with a tricyclic antidepressant. These three patients suggest that opiate agonists may have some effects on underlying psychopathology, although other more psychosocial interpretations are equally tenable.

I claim:

1. The method of eliminating the withdrawal symptoms in an opiate-addicted human who has had methadone treatment, which comprises orally administering to said human an effective amount of 2-(2,6-dichloroanilino)-2-imidazoline or a non-toxic, pharmaceutically acceptable acid addition salt thereof.

2. The method of claim 1, where said effective amount is 5 to 15 μg/kg.

* * * * *

UNITED STATES PATENT AND TRADEMARK OFFICE
CERTIFICATE OF CORRECTION

PATENT NO. : 4,312,878
DATED : January 26, 1982
INVENTOR(S) : DONALD E. REDMOND, JR. ET AL.

It is certified that error appears in the above—identified patent and that said Letters Patent is hereby corrected as shown below:

Title page, [75], this paragraph should read:

-- Inventors: Donald E. Redmond, Jr., Hamden, Conn.; Mark S. Gold, Warren Township, New Jersey; Herbert D. Kleber, North Haven, Conn. --

Column 2, 3rd line from bottom: "chonidine" should read -- clonidine --.

Signed and Sealed this

Sixth Day of July 1982

[SEAL]

Attest:

GERALD J. MOSSINGHOFF

Attesting Officer

Commissioner of Patents and Trademarks